United States Patent
Kurita

[11] Patent Number: 5,897,511
[45] Date of Patent: Apr. 27, 1999

[54] ORGANISM VIBRATION MEASURING DEVICE AND METHOD

[75] Inventor: Masahiro Kurita, Tokyo, Japan

[73] Assignee: Institute of SRS, Tokyo, Japan

[21] Appl. No.: 08/936,542

[22] Filed: Sep. 24, 1997

[30] Foreign Application Priority Data

Sep. 26, 1996 [JP] Japan .................................. 8-254822

[51] Int. Cl.⁶ .................................................. A61B 5/00
[52] U.S. Cl. ............................................................ 600/595
[58] Field of Search ................................... 600/552, 587, 600/595, 9, 13, 14

[56] References Cited

U.S. PATENT DOCUMENTS

| | | | |
|---|---|---|---|
| 4,665,928 | 5/1987 | Linial et al. | 600/595 |
| 4,928,709 | 5/1990 | Allison et al. | 600/595 |
| 5,140,994 | 8/1992 | Campbell et al. | 600/595 |
| 5,183,056 | 2/1993 | Dalen et al. | 600/595 |

*Primary Examiner*—Max Hindenburg

[57] ABSTRACT

An organism vibration measuring device is for measuring a vibration of a portion of an organism which is put in an alternating magnetic field. The organism vibration measuring device includes a vibration detecting member, having a structure suitable for attachment to the portion of the organism, for detecting the vibration of the portion of the organism which resonates under an influence of the alternating magnetic field. It further includes a vibration measuring member for measuring the vibration state of the portion of the organism on the basis of a detection signal from the vibration detecting member.

11 Claims, 2 Drawing Sheets

ORGANISM VIBRATION MEASURING DEVICE AND METHOD

BACKGROUND OF THE INVENTION

1. Field of the Invention

The invention relates to an organism vibration measuring device and an organism vibration measuring method, for measuring vibrations of a portion of an organism which is put in an alternating magnetic field and resonates under the influence of the alternating magnetic field.

2. Description of Related Art

In these modern days, there is growing a social interest with respect to the adverse effects of electromagnetic waves, generated by portable telephones, personal computers, television sets, domestic appliances, and high voltage transmission lines, on human bodies. It has been found that in a case where a human body is put in a magnetic field generated by the electromagnetic waves, it is affected by the magnetic field to become irregular according to the strength of the magnetic field, and the degree of the irregularity varies from person to person even if the magnetic field is of the same strength.

However, there is conventionally neither an art of measuring the degree of effects on the organism by the alternating magnetic field, nor an art of analyzing the effects on the human body according to the degree of the effects.

SUMMARY OF THE INVENTION

Muscles are moved by an electric signal from the nerves and are mechanically contracted according to the movement of various ions. Therefore, it can be imagined that various electromagnetic forces may act on the muscles themselves also in a case where a human body is put in a fluctuated magnetic field. However, it is technically difficult to carry out detection of the effects thereof from the electromagnetic point of view.

Therefore, in order to achieve the invention, the inventors intended to study, as follows.

First, measuring the dynamic movement of a portion of an organism (e.g. a finger of a human body) other than the electromagnetic phenomenon was studied with the attention paid upon a spatial movement of the portion of the organism.

Second, the inventors considered that the muscles might periodically undergo dynamic effects according to a periodical movement of the electromagnetic field, and that if it would be correct, the change of the dynamic effects generated in the muscles would be reasonably measured by using an accelerometer.

Third, the inventors considered that because the muscle system was surrounded by a skin not to be exposed on the body surface, it would be difficult to distinguish the spatial movement of the muscles from the movement of the skin or of the subcutaneous tissue by attaching an acceleration sensor outside the body (to the surface of the skin). Therefore, the inventors considered to detect "an individual muscular movement" as "an indirect movement of a finger", with the object surrounded by using a plastic ring or the like which did not cause the spatial movement due to the movement of the magnetic field.

As a result of the earnest study and research, the inventors discovered the phenomenon in which the organism, especially the muscles of the organism resonate under the influence of the alternating magnetic field. Such a phenomenon was not known in the past, and therefore there was not a device nor a method, for measuring such a phenomenon in the past either.

On the basis of the discovery, the present inventors have found that the measurement of the organism which resonates under the influence of the alternating magnetic field, for the purpose of analyzing the degree of the influence of the alternating magnetic field on the organism, can reveal the degree of the resonance of the organism according to the strength of the alternating magnetic field, and the individual difference of the degree of the resonance on the organism according to the alternating magnetic field of the same strength.

The invention has been developed in view of the above-mentioned circumstances. Therefore, an object of the invention is to provide an organism vibration measuring device which is capable of measuring a vibration of an organism which resonates under the effect of an alternating magnetic field. Another object of the invention is to provide an organism vibration measuring method which is capable of measuring such a vibration of an organism.

That is, in accordance with one aspect of the present invention, the organism vibration measuring device for measuring a vibration of a portion of an organism which is put in an alternating magnetic field, comprising: a vibration detecting member having a structure suitable for attachment to the portion of the organism, for detecting the vibration of the portion of the organism which resonates under an influence of the alternating magnetic field; and a vibration measuring member for measuring a state of the vibration of the portion of the organism on the basis of a detection signal from the vibration detecting member.

According to the organism vibration measuring device having such a structure, it is possible to measure the vibration condition of the organism which is put in the alternating magnetic field and resonates under the effects of the alternating magnetic field. Further, such a measurement is useful to provide a personal index showing the degree of the reactivity of the electromagnetism of the organism, and the irritability of the organism, and the variability thereof with the passage of time.

Further, the measurement is useful for detecting the persons who are heavily hypersensitive to the electromagnetic field (medically, referred to as "electromagnetic wave hypersensitiveness"). It is suggested that the measurement can be used to provide an organism index when subjecting a remedial approach to the relevant persons. Accordingly, the above measurement is expected to be a measuring method of social deep significance.

As to the portion of the organism, any portion of the organism may be available, for example, a finger, an arm or the like, insofar as it can vibrate under the influence of the alternating electromagnetic field.

In the organism vibration measuring device of the invention, although an alternating magnetic field generator for generating the alternating magnetic field may not be necessarily provided as a constituent element, it is preferable to further comprises the alternating magnetic field generator. Accordingly, it is possible to use the organism vibration measuring device easily.

Although any portion of the organism may be used for measuring the vibration thereof, it may be a finger. In this case, the vibration detecting member may have a ring suitable for attachment to a finger.

As to the vibration detecting member in the organism vibration measuring device, any detector may be employed insofar as it is capable of detecting the vibration of the organism. For example, the vibration detecting member may comprise an acceleration sensor. The vibration detecting member may comprise a ring suitable for attachment to a finger and an acceleration sensor attached to the ring.

Preferably, the organism vibration measuring device further comprises an analyzing device for analyzing an effect of the magnetic field on the portion of the organism on the basis of measured results by the vibration measuring member.

In accordance with another aspect of the present invention, the organism vibration measuring method for measuring a vibration of a portion of an organism, comprises the steps of; putting the portion of the organism in an alternating magnetic field, resonating the portion of the organism under an influence of the alternating magnetic field, detecting vibration of the portion of the organism, and determining a vibration state of the portion of the organism on the basis of the detected vibration thereof.

According to the organism vibration measuring method, it is possible to measure the vibration condition of the organism which is put in the alternating magnetic field and resonates under the effects of the alternating magnetic field. Further, such a measurement is useful to provide a personal index showing the degree of the reactivity of the electromagnetism of the organism, and the irritability of the organism, and the variability thereof with the passage of time.

Further, the measurement is useful for detecting the persons who are heavily hypersensitive to the electromagnetic field (medically, referred to as "electromagnetic wave hypersensitiveness"). It is suggested that the measurement can be used to provide an organism index when subjecting a remedial approach to the relevant persons. Accordingly, the method is expected to be a measuring one of social deep significance.

The portion of the organism may be a muscle of a finger. Preferably, the organism vibration measuring method further comprises a step of analyzing an effect of the magnetic field on the portion of the organism, on the basis of the determined vibration state of the portion of the organism.

BRIEF DESCRIPTION OF THE DRAWINGS

The present invention will become more fully understood from the detailed description given hereinbelow and the accompanying drawings which are given by way of illustration only, and thus are not intended as a definition of the limits of the present invention, and wherein.

PREFERRED EMBODIMENT OF THE INVENTION

Figure 1:
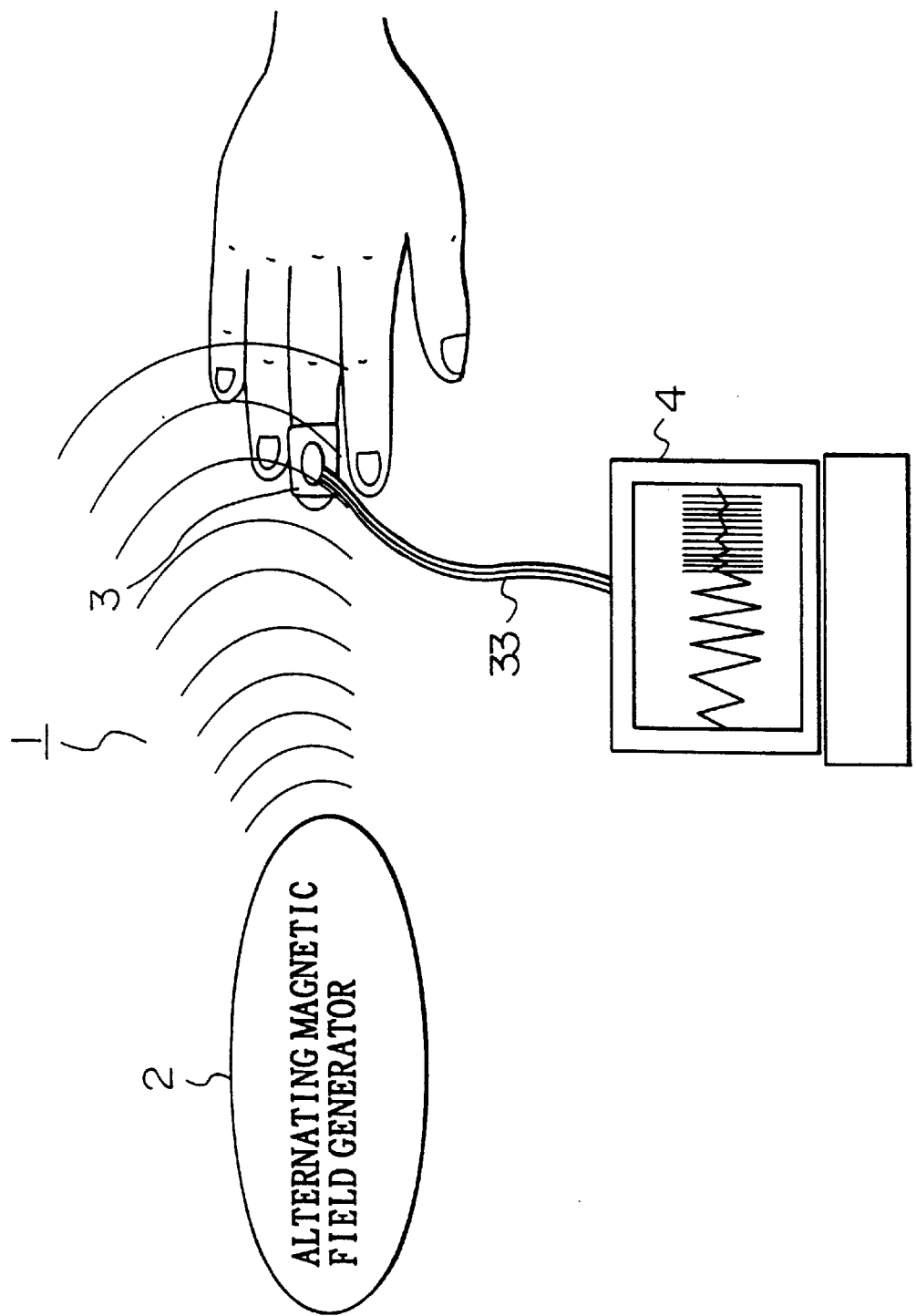
FIG. 1 is a schematic view showing a general arrangement of the organism vibration measuring device according to an embodiment of the invention.
Figure 2:
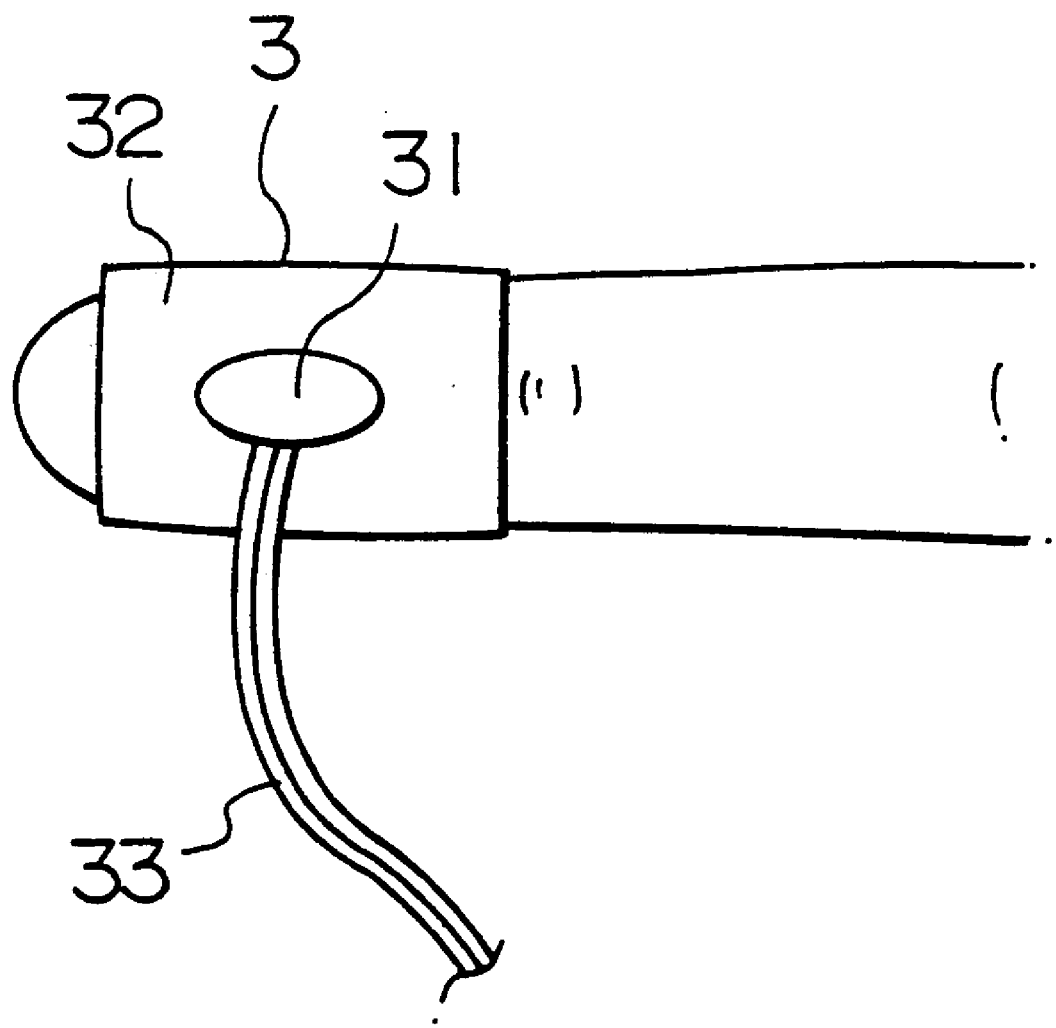
FIG. 2 is an enlarged view of a vibration detecting member attached to a finger.

An organism vibration measuring device according to an embodiment of the invention, and an organism vibration measuring method according to an embodiment of the invention will be described with reference to FIGS. 1 and 2. FIG. 1 is a schematic view showing a general arrangement of the organism vibration measuring device according to an embodiment of the invention, and FIG. 2 is an enlarged view of a vibration detecting member attached to a finger.

An organism vibration measuring device 1 according to the embodiment comprises an alternating magnetic field generator 2, a vibration detecting member 3 attached to a portion of an organism, e.g. a finger of a person, for detecting vibrations of the portion of the organism, and a vibration measuring member 4 for receiving the signals detected by the vibration detecting member 3 to measure the vibration condition of the organism, as shown in FIG. 1. In a case where the portion of the organism to be measured is a finger, it is preferable to provide a fixing member for fixing a wrist so as not to move, such as a band, a member for fixing the wrist by one-operation or the like, which is not shown. Such a fixing member makes it easy to carry out the measurement.

As the alternating magnetic field generator 2, any member may be employed insofar as it is capable of generating an alternating magnetic field, such as an AC electromagnet. The alternating magnetic field generator 2 is preferably provided with a generator movement member for moving the alternating magnetic field generator 2 to adjust the distance between the magnetic field generator 2 and the portion of the organism to be measured. Preferably, the strength of the alternating magnetic field produced by the alternating magnetic field generator 2 can be adjusted. The magnetic field generator 2 comprises an AC electromagnet. The strength (gauss) of the alternating magnetic field produced by the generator 2 at spatial positions which are spaced predetermined distances in predetermined directions from a reference point, are previously measured and known, with respect to a plurality of electric currents with specific frequencies.

The alternating magnetic field generator 2 is not necessarily provided as a constituent element of the organism vibration measuring device 1, therefore it may be provided separately from the organism vibration measuring device 1.

As the portion of the organism, any portion may be available insofar as it is a portion of the organism. In the case where the organism is a portion of a human body, preferably, a finger may be adopted as the portion of the organism because the muscles of a finger are easily vibrated in response to the alternating electromagnetic field.

As the vibration detecting member 3, any member may be employed so long as the member can be attached to the portion of the organism and can detect the vibration of the portion of the organism. For example, a well-known acceleration sensor is preferably utilized. The acceleration sensor 31 preferably has a code 33 which is electromagnetically shielded. The acceleration sensor 31 has enough sensitomety to enable measurement over 200 times per one second, in order to detect the waveform of the muscular movement which depends on the change of the magnetic field corresponding to the frequency of 50 Hz or 60 Hz, used for the commercial electric power. The measurement is carried out by defining the half-waveform of the spatial movement at four points or more.

Further, the vibration detecting member 3 is provided with an attachment member 32 which is adapted to be detachably attached to the portion of the organism. In this embodiment, because the portion of the organism which is the object for detection of the vibration is a finger, the attachment member 32 is preferably comprised of a ring which can be easily attached to or detached from the finger. Any other construction may be employed, insofar as it can be attached thereto or detached therefrom. In a case where the attachment member 32 is a ring, the sectional shape of the attachment member 32 is preferably a C-shape so as to enable deformation thereof according to the thickness of a finger. The material of the attachment member 32 is not limited particularly; however, it is preferably made of non-conductive plastic.

As the vibration measuring member 4, although any device may be employed so long as the device enables measurement of the vibration, preferably, the vibration measuring member 4 is provided with a display for displaying the waveform of the vibration on a screen thereof because the vibration condition is visible in real time and easy to know.

The vibration measuring device 4 may be comprised of a printer which is capable of printing the waveform of the vibrations, or may be adapted to connect with a printer.

Further, the vibration measuring device 4 not only measures the vibration of the organism but also may be comprised of an analyzing device for analyzing the influence of the electromagnetic field on the organism on the basis of the measurement of the organism vibration.

The transmission of the signal from the vibration detecting member 3 to the vibration measuring member 4 may be carried out by a wire communication using a cord 33 or the like, or may be carried out by a wireless communication using a transmitter (not shown) and a receiver (not shown).

Next, an example of the handling manner of the organism vibration measuring device 1 having the above-described structure and the operation thereof will be explained, as follows.

First, in a case where a wrist fixing member is provided, the wrist is fixed by the wrist fixing member, then the vibration detecting member 3 is attached and fixed to a finger through the attachment member 32 having a ring-shape, a cap-shape or the like. Next, the alternating magnetic generator 2 and the vibration measuring device 4 are operated. An electric power used for the alternating magnetic field generator 2 has a predetermined frequency, e.g., 50 Hz, 60 Hz or the like.

Thereafter, the strength of electromagnetic field in the vicinity of the finger is raised by adjusting the position of the alternating magnetic field generator 2 and the strength of the electromagnetic field generated thereby, while watching the screen of the vibration measuring member 4, or the like. As the strength of electromagnetic field in the vicinity of the finger is raised, the finger starts to vibrate at a certain one.

The vibration starting point of the finger can be clearly recognized on a monitor. It is also possible to determine the vibration starting point by extracting the specific frequency components by the Fourier analysis and using the strength on the power spectrum thereof, as occasion demands. The distance between the alternating magnetic field generator 2 and the finger, at which the finger starts to vibrate, is used as an index. The distance is called "resonance threshold value distance". Because the strength of the magnetic field exhibited at this distance can be previously measured, it is also possible to evaluate the vibration of the finger by using the magnetic field.

The alternating magnetic field varies according to the frequency of the electric power applied to the alternating magnetic field generator 2. The varied alternating magnetic field acts on the muscles of the finger. Thereby, the finger vibrates according to the variation of the alternating magnetic field. The vibration of the finger is detected by the vibration detecting member 3, the detected signal is transmitted to the vibration measuring member 4, then the vibration measuring member 4 measures the vibration condition of the finger on the basis of the transmitted signal, and the measured result is shown on the screen of the vibration detecting member 4, or the like, for example, as a vibration waveform. It is possible to analyze the influence of the magnetic field to the organism by seeing the measured results such as the waveform and the like.

In a case where the vibration measuring member 4 is provided with a member for analyzing the influence of the magnetic field on the basis of the measured results of the vibration, not only the measurement of the vibration but also the analyzation thereof can be carried out.

Therefore, according to the embodiment of the invention, the vibration of the organism which vibrates under the influence of the alternating electromagnetic field generated by the alternating electromagnetic field generator 2 can be measured by the vibration detecting member 3 attached to a portion of the organism and the vibration measuring member 4 for receiving the signal detected by the vibration detecting member 3 to measure the vibration condition of the portion of the organism. Accordingly, the measurement is useful to provide a personal index showing the degree of reactivity or irritability, to the electromagnetism of the organism, and the variability thereof with the passage of time.

Further, the above measuring device enables a simple and convenient measurement which exerts no adverse effect on the organism and enables repeated measurements.

Further, the measurement is useful for detecting the persons who are heavily hypersensitive to the electromagnetic field (medically, referred to as "electromagnetic wave hypersensitiveness"). It is suggested that the measurement can be used to provide an organism index when subjecting a remedial approach to the relevant persons. Accordingly, the above measurement is expected to be a measuring method of social deep significance.

MEASUREMENT EXAMPLE 1

A measurement was carried out on 27 adults, while applying the alternating electromagnetic field having a frequency of 50Hz to the middle fingers of their right hands. The measured values are shown hereinbelow, where the magnetic field on the surface of the electromagnet is set to 500 gausses.

The measurements were repeatedly carried out for two days in order to know the repeatability and the consistency of the measured resonance forces, and the variation due to training.

The first, second, third, and fourth measurements were carried out on the morning of the first day, on the morning of the second day, on the afternoon of the second day, and on the evening of the second day, respectively. The objects were divided into three groups, and the divided three groups were assigned for the second, third and fourth measurements, respectively.

As a result, the average value (±standard deviation) of the resonance threshold value distances (d) was represented by $d=5.2$ ($\pm 2.0$) in cm in the first measurement. In the other measurements, the average value (d) were represented by the followings:

$d=6.3$ ($\pm 1.0$) in the second measurement, $d=5.8$ ($\pm 1.1$) in the third measurement, and $d=6.6$ ($\pm 1.6$) in the fourth measurement.

In any one of the groups, the average value is increased in comparison with the first measurement, which shows the averages are significantly increased from the statistical point of view (the statistical significance levels are represented by $p<0.001$, $p<0.03$, $p<0.02$). The total average value of the second day is represented by $d=6.3$ ($\pm 1.2$), which is significantly increased from the measured value at the first measurement (the significance level is represented by $p<0.003$). The statistical significance is determined by applying a standard method called "t-test" to the corresponding data set, and the significance level is represented by a numerical value which is calculated as the probability of judging wrongly.

On this occasion, the correlation between the value of "d" and another organism index was also investigated. As a result, it has been found that the value of "d" is correlated with the electric current value of the threshold value (for the spasm of the muscles) at which the muscles are contracted when the electric current having a low frequency of 30 Hz is percutaneously flowed (the correlation coefficient r is represented by r=0.341 for the data of 34 persons).

The correlation coefficient is a numerical value showing a statistical ground of determining whether or not the data set related to two kinds of phenomena are correlated to each other. In a case where the number of the data is 34 pairs, the above numerical value can be determined to have a significant correlativity.

MEASUREMENT EXAMPLE 2

In this example, the measurement was performed similar to the Measurement Example 1, for 47 persons of another adult group.

The measured result shows that the average value is 4.7 (±2.0) cm. In this group, there were investigated the correlation with the difference between male and female, the dependency to age, and the bloodstream in the fingertip skin. As a result, there was recognized no correlation with the difference between male and female, and with the dependency to age, whereas there was shown a positive correlation with the bloodstream in the fingertip skin.

Any one of the contents of the Measurement Examples 1 and 2 is a new knowledge which has not been announced before.

Physiological and social significance of the present measuring method would be understood from the measured result, as follows.

It is understood that the measured values include "individual difference" from Measurement Examples 1 and 2.

It is understood that the measured value are physiologically "significant indices", from the correlation with the muscles contracting threshold value shown in the Measurement Example 1, and the correlation with the bloodflow in the skin shown in the Measurement Example 2.

The Measurement Example 1 shows that the measurement values have the consistency and vary due to a certain training.

According to the above-mentioned results, the measurement value due to electromagnetic waves from portable telephones, personal computers, television sets, domestic appliances, high voltage transmission lines, or the like is useful to provide a personal index showing the degree of reactivity or irritability, to the electromagnetism of the organism, and the variability thereof with the passage of time.

Further, the above measurement enables a simple and convenient measurement which exerts no adverse effect on the organism and enables repeated measurements.

Further, the measurement is useful for detecting the persons who are heavily hypersensitive to the electromagnetic field (medically, referred to as "electromagnetic wave hypersensitiveness"). It is suggested that the measurement can be used to provide an organism index when subjecting a remedial approach to the relevant persons. Accordingly, it is considered that the measurement is one of social deep significance. The invention being thus described, it will be obvious that the same way be varied in many ways. Such variations are not to be regarded as a departure from the spirit and scope of the invention, and all such modifications as would be obvious to one skilled in the art are intended to be included within the scope of the following claims.

What is claimed is:

1. An organism vibration measuring device for measuring a vibration of a portion of an organism which is put in an alternating magnetic field, comprising:

a vibration detecting member, suitable for attachment to the portion of the organism, for detecting the vibration of the portion of the organism which resonates under an influence of the alternating magnetic field; and a vibration measuring number for measuring a state of the vibration of the portion of the organism on the basis of a detection signal from the vibration detecting member.

2. An organism vibration measuring device as claimed in claim 1, further comprising an alternating magnetic field generator for generating the alternating magnetic field.

3. An organism vibrating measuring device as claimed in claim 2, wherein the alternating magnetic field generator comprises an AC electromagnet.

4. An organism vibration measuring device as claimed in claim 1, wherein the vibration detecting member includes a ring suitable for attachment to a finger, the finger being the portion of the organism.

5. An organism vibrating measuring device as claimed in claim 1, wherein the ring is made of non-conductive material and includes a C-shaped section.

6. An organism vibration measuring device as claimed in claim 1, wherein the vibration detecting member comprises an acceleration sensor.

7. An organism vibration measuring device as claimed in claim 1, wherein the vibration detecting member comprises a ring suitable for attachment to a finger, the finger being the portion of the organism, and an acceleration sensor attached to the ring.

8. An organism vibration measuring device for measuring a vibration of a portion of an organism which is put in an alternating magnetic field, comprising:

vibration detecting means for detecting the vibration of the portion of the organism which resonates under an influence of the alternating magnetic field; and vibration measuring means for measuring a state of the vibration of the portion of the organism on the basis of a detection signal from the vibration detecting means.

9. An organism vibration measuring method for measuring a vibration of a portion of an organism, comprising the steps of:

subjecting the portion of the organism to an alternating magnetic field;

resonating the portion of the organism under an influence of the alternating magnetic field;

detecting vibration of the portion of the organism; and determining a vibration state of the portion of the organism on the basis of the detected vibration.

10. An organism vibration measuring method as claimed in claim 9, wherein the portion of the organism is a muscle of a finger.

11. An organism vibration measuring method as claimed in claim 9, further comprising a step of analyzing an effect of the magnetic field on the portion of the organism, on the basis of the determined vibration state of the portion of the organism.

* * * * *